United States Patent [19]

Ramachandran et al.

[11] Patent Number: 4,849,538
[45] Date of Patent: Jul. 18, 1989

[54] PROCESS FOR THE PRODUCTION OF NITRILES

[75] Inventors: Ramakrishnan Ramachandran, Allendale; Donald L. MacLean, Annandale; Donald P. Satchell, Jr., Summit, all of N.J.

[73] Assignee: The BOC Group, Inc., Murray Hill, N.J.

[21] Appl. No.: 215,858

[22] Filed: Jul. 6, 1988

Related U.S. Application Data

[63] Continuation-in-part of Ser. No. 172,112, Mar. 23, 1988, abandoned.

[51] Int. Cl.$^4$ .......................................... C07C 120/14
[52] U.S. Cl. .................................... 558/319; 558/320
[58] Field of Search .............................. 558/319, 320

[56] References Cited

U.S. PATENT DOCUMENTS

| | | | |
|---|---|---|---|
| 3,161,670 | 12/1964 | Adams et al. | 558/319 X |
| 3,176,444 | 4/1965 | Kiyonaga | 55/26 |
| 3,591,620 | 7/1971 | Yoshino et al. | 260/465.3 |
| 4,070,393 | 1/1978 | Angstadt et al. | 558/319 X |
| 4,305,886 | 12/1981 | Pujado | 558/320 X |
| 4,335,056 | 6/1982 | Callahan et al. | 260/465.3 |
| 4,498,910 | 2/1985 | Benkmann | 55/18 |
| 4,609,502 | 9/1986 | Khoobiar et al. | 260/465.3 |
| 4,754,049 | 6/1988 | Khoobiar et al. | 558/320 |

OTHER PUBLICATIONS

Gates et al.; "Chemistry of Catalytic Processes", (1979), McGraw-Hill, pp. 349–350 and 380–384.
Thomas; "Catalytic Processes and Proven Catalysts", (1970), Academic Press, pp. 118–119.
Pujado et al.; "Catalytic Conversion of L.P.G.", (1986), American Institute of Chem. Eng., pp. 1–19, drawings and tables.

Primary Examiner—Joseph Paul Brust
Attorney, Agent, or Firm—Carol A. Nemetz; R. Hain Swope; Larry R. Cassett

[57] ABSTRACT

An improved process is provided for the production of nitriles from hydrocarbons by reaction with oxygen, air or a gas enriched in oxygen relative to air, preferably the latter, and ammonia in the presence of an ammoxidation catalyst. An alkane, e.g. propane, is converted to an alkene in a dehydrogenator. The product stream is introduced into an ammoxidation reactor. The product formed therein is recovered in a conventional quench tower. The gaseous effluent from the quench tower is treated in a PSA unit to form a gas stream containing the unreacted alkane and alkene as well as a minor amount, i.e. less than about 1 percent by volume, of oxygen and nitrogen, if present in the feed to the ammoxidation reactor. The gas stream, which may or may not contain hydrogen depending on the absorbent in the PSA unit, is introduced into a selective oxidation unit to remove the remaining oxygen and then recycled to the dehydrogenator. Hydrogen may be introduced into or removed from the PSA effluent, depending on the function of the adsorbent therein, to obtain an optimum concentration for introduction into the dehydrogenator. A particularly preferred PSA system for use in the subject process comprises two parallel PSA units containing different adsorbents such that the gas stream formed in one contains all of the hydrogen in the gas phase from the quench tower. The feed to the PSA units is divided disproportionately so that the combined PSA effluent recycle streams contain the optimum concentration of hydrogen for the dehydrogenator.

15 Claims, 3 Drawing Sheets

PROCESS FOR THE PRODUCTION OF NITRILES

RELATED APPLICATIONS

This application is a continuation-in-part of U.S. patent application Ser. No. 172,112, filed Mar. 23, 1988, now abandoned.

The present invention is directed to a process for producing nitriles from alkanes, an oxygencontaining gas and ammonia in the presence of a suitable catalyst under conditions which achieve high efficiency and selectivity toward the desired product.

BACKGROUND OF THE INVENTION

The production of nitriles by ammoxidation of an appropriate alkene in the presence of a suitable catalyst is well known. The Production of acrylonitrile, for example, from a gaseous feed of propylene, ammonia and air is described by Bruce E. Gates et al in *Chemistry of Catalytic Processes*, McGraw-Hill (1979), pp. 380–384.

The feed is sent to an ammoxidation reactor where, in the presence of a suitable catalyst, acrylonitrile is produced along with lesser amounts of other nitrogen-containing compounds. The effluent from the ammoxidation reaction is quenched with water and the desired products are obtained in the liquid phase. The gas phase by-Products, typically oxygen, carbon dioxide, carbon monoxide, nitrogen and unreacted hydrocarbon, are combined with natural gas and sent to a boiler for combustion as disclosed, for example, in Yoshino et al., U.S. Pat. No. 3,591,620 and Callahan et al., U.S. Pat. No. 4,335,056.

More recently, Khoobiar et al., in U.S.. Pat. No. 4,609,502 disclosed a cyclic process for producing acrylonitrile using propane as a starting material which is initially dehydrogenated catalytically in the presence of steam to form propylene. This is in contrast to most conventional dehydrogenation processes and which avoid steam primarily due to the costs involved. After ammoxidation, the effluent is quenched, the desired product removed, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are by-products of dehydrogenation, and unreacted propylene in addition to carbon oxides. As an option, this gas mixture is split and a portion is sent to a separator which removes only carbon dioxide. A portion of the effluent from the separator is purged to remove light hydrocarbons. The nonpurged stream is mixed with the remainder of the oxidator effluent, fresh propane and steam, if necessary, sent to the dehydrogenator where the propane is converted to propylene. Another option is to cool and liquify the $C_3$ hydrocarbons therefrom and then vaporize them prior to recycle.

The aforementioned process suffers from several disadvantages. For example, there is no practical way to selectively remove by-products of propane dehydrogenation, such as methane, ethane, ethylene and the like, thereby preventing their accumulation in the system other than by removing them in the purge stream. The removal of these gases in a purge stream will result in a loss of some of the circulating propane and propylene. As the process is being carried on in a continuous manner, this loss of starting material causes a significant decrease in the yield of propylene. As mentioned above, propane and propylene can be recovered from the purge stream prior to venting. This requires additional refrigeration apparatus to cool and liquify propylene and propane. The separated $C_3$ hydrocarbons must be vaporized prior to recycle. These operations add to the capital costs and power requirements of the process.

Another disadvantage of the Khoobiar et al process stems from the use of the selective oxidation reactor to treat the gaseous effluent from the quencher. The gases exiting the quencher are at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three options to alleviate this problem. First, the amount of oxygen entering the oxidation reactor can be reduced by other means. Second, multiple reactors can be utilized with a cooling means between each pair of reactors. Third, a portion of the effluent from the reactor is passed through a cooling means and recycled to the feed to reduce the internal temperature of the reactor. None of these measures is attractive from the viewpoint of cost and efficiency.

The oxidation reactor in the Khoobiar et al process is operated with oxidation catalysts such as noble metals (e.g., platinum). Olefins and carbon monoxide, which are generated in the dehydrogenation reactor, are known to deactivate these catalysts, as disclosed in *Catalytic Processes and Proven Catalysts*. Charles L. Thomas, Academic Press (1970) pp. 118–119. Accordingly, multiple oxidation reactors must be used to allow for frequent regeneration of the catalyst which represents yet another addition to production costs (U.S. Pat. No. 4,609,502, column 4, lines 51–56).

It is therefore apparent that the industry is still searching for a cost effective process of converting hydrocarbons into nitriles. Applicants have discovered a process which is cost effective and in which the disadvantages of the aforementioned systems are substantially reduced or eliminated. Moreover, in comparison to conventional processes, the thermal requirements of Applicants' process are markedly reduced.

SUMMARY OF THE INVENTION

A process is disclosed for the production of nitriles comprising converting a gaseous alkane to the corresponding alkene in a dehydrogenator, reacting the alkene in an ammoxidation reactor with an oxygen-containing gas, preferably oxygen-enriched air, and ammonia gas in the presence of an ammoxidation catalyst to form the desired product. The product stream is quenched with a liquid to form a liquid phase containing the desired product and a gas phase which is passed under pressure into a pressure swing adsorption unit to remove carbon oxides, oxygen, nitrogen, and lower hydrocarbons therefrom. The product stream from the pressure swing adsorption unit is passed into a selective oxidation unit where the remainder of the oxygen is removed. The effluent from the selective oxidation unit is recycled to the dehydrogenator with fresh propane feed.

DESCRIPTION OF THE PREFERRED EMBODIMENTS

The process of this invention is applicable to the synthesis of nitriles. In each instance, an alkene is reacted with an oxygen-containing gas comprising pure oxygen, air or a gas enriched in oxygen relative to air in the presence of a suitable catalyst The term "suitable catalyst" indicates a catalyst that will catalyze the production of the desired product under the conditions utilized in the reactor. In the subject process, the catalyst is an ammoxidation catalyst. These catalysts and their use are conventional and well known to one of ordinary skill in the art.

Illustrative of products, and their respective starting gaseous alkanes, which can be advantageously produced by the method of this invention are acrylonitrile from propane, methacrylonitrile from isobutane, ethylene oxide and the like. In the interest of brevity, the subject process will be described with reference to the production of acrylonitrile from propane, but is in no way intended to be limited thereto.

Figure 1:
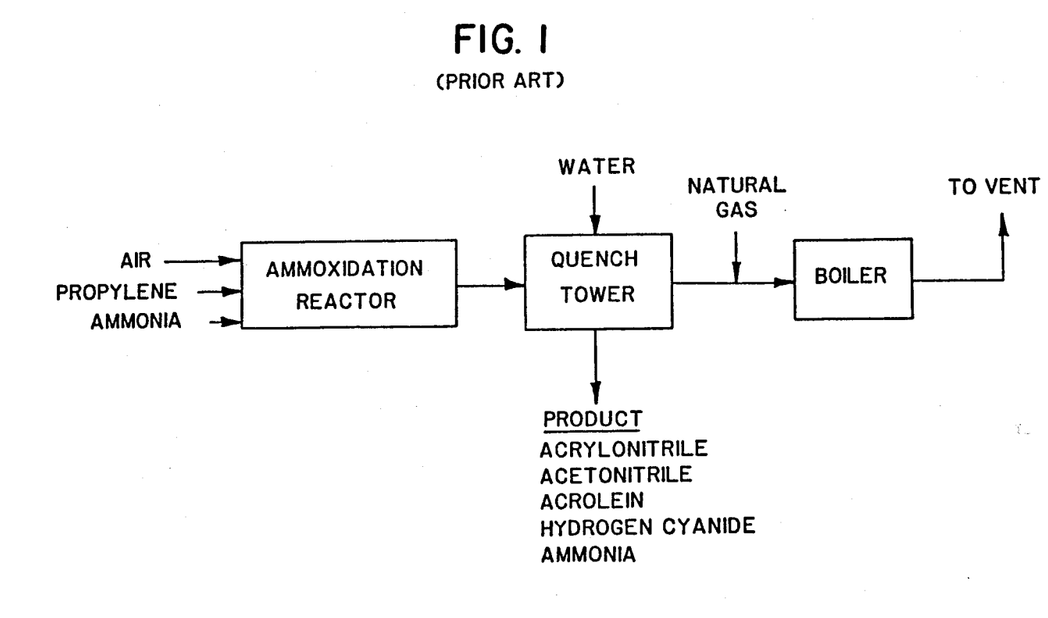
FIG. 1 illustrates in a block diagram a present conventional process of producing acrylonitrile.

Turning to the drawings, a process currently utilized commercially to produce acrylonitrile is illustrated in FIG. 1. Propylene, ammonia and air are fed into a conventional reactor containing a suitable ammoxidation catalyst. The reactor may be of any conventional fixed or fluidized bed design, typically the latter. Such processes, which do not involve a recycle step utilize air or oxygen-enriched air in the reactor feed, although air is normally used for reasons of economy The oxygen concentration in the reactor feed is not considered to be critical since there is no problem with accumulation of other gases, primarily nitrogen, in the system due to the lack of recycle. Those skilled in the art are aware the oxygen content in the feed of such a process must be regulated in regard to other aspects of the process.

The reactor product gases are cooled in a heat exchanger, not shown, to form steam and then passed to a water quench column or tower to dissolve the products, i.e. acrylonitrile, acetonitrile, acrolein and hydrogen cyanide, as well as unreacted ammonia. The acrylonitrile is subsequently recovered from the aqueous solution by conventional methods. The off-gases from the quench tower are combined with natural gas and combusted in a boiler to generate steam. The off-gases of the boiler are vented. Since there is no recycle provided in such a process, the yield of acrylonitrile realized is directly related to the efficiency of the reactor.

Figure 2:
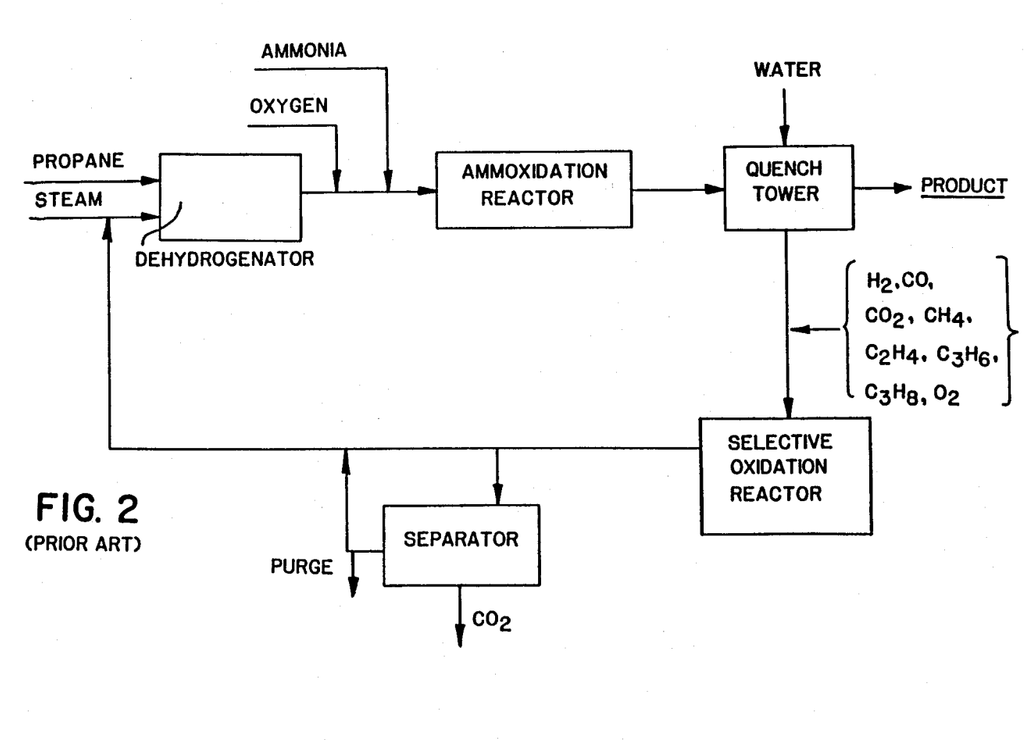
FIG. 2 illustrates in a block diagram a prior art process of producing acrylonitrile utilizing a recycle step.

FIG. 2 illustrates the cyclic process for producing acrylonitrile disclosed in Khoobiar et al U.S. Pat. No. 4,609,502. In this process, propane and steam are fed into a dehydrogenator to form propylene which is then mixed with oxygen and ammonia and fed into an ammoxidation reactor such as described in FIG. 1. The product is fed to an aqueous quench tower as in FIG. 1 and the products withdrawn in solution. The gaseous take-off from the quench tower, typically containing oxygen, hydrogen, carbon monoxide, carbon dioxide, methane, ethane, ethylene, propane and propylene, is fed to a selective oxidation reactor. As previously indicated, it is generally essential for the efficient operation of such a reactor to heat the gas mixture prior to introduction therein.

A portion of the off-gas from the oxidation reactor is passed to a separator to remove carbon oxides by an undisclosed mechanism. A portion of the separator effluent, which contains light hydrocarbons and hydrogen, is purged, treated to remove propane and propylene and discarded thereby preventing buildup of by-products in the system. The propane and propylene are combined with the remainder of the oxidator effluent and the remainder of the separator effluent and recycled to the dehydrogenator. It is, of course, necessary for the oxidator to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 3:
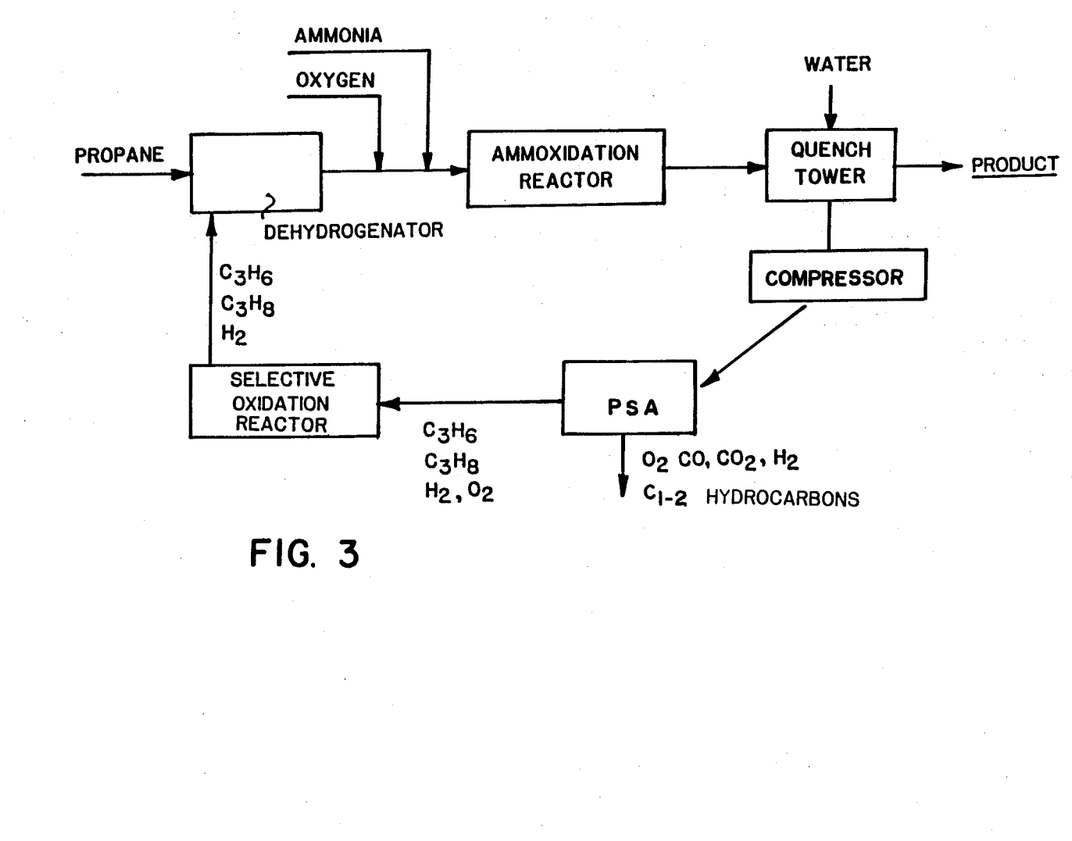
FIG. 3 illustrates in a block diagram the process of the invention for producing acrylonitrile.

The process of the present invention is illustrated in FIG. 3. The present process provides the efficiency of recycle afforded by the process illustrated in FIG. 2 and is similar in a generic sense in that it contains the same kinds of functional units, yet is substantially more efficient and, unexpectedly, capable of effectively utilizing air or oxygen-enriched air as a feed to the ammoxidation reactor. Specifically, the subject process utilizes a pressure swing adsorption unit to effectively remove carbon oxides, nitrogen, oxygen, hydrogen and light hydrocarbons from the quench tower effluent. Therefore, the selective oxidation reactor can be comparatively small in terms of capital expenditure and have a long life, yet still effectively remove the minor amount, i.e. less than 1 percent by volume, of oxygen from the recycle feed to the dehydrogenator. The configuration of the subject process eliminates the substantial loss of efficiency inherent in the process of FIG. 2 by the use of the purge stream. Further, it is not contemplated in the present process to utilize steam in the dehydrogenator, thereby providing an additional saving of energy.

Referring to FIG. 3, propane is fed into the dehydrogenator where it is converted to propylene. For increased catalyst life, it is preferred to introduce a hydrogen containing gas into the dehydrogenator with the propane feed. The required amount of hydrogen can conveniently be provided through the recycle stream from the PSA unit as will be discussed below. The hydrogen-containing gas can, if desired, be provided as a discrete stream. The catalyst utilized in the dehydrogenator can be any conventional dehydrogenation catalyst, preferably one or more Group VIII noble metals such as platinum on an alumina support. The effluent product stream from the dehydrogenator comprising unreacted propane, propylene and hydroqen, is fed into a conventional ammoxidation/ oxidation reactor along with pure oxygen, air or, preferably, oxygen-enriched air and ammonia.

The ammoxidation reactor utilized in the present process is conventional and may employ either a fixed or fluidized catalyst bed. A typical example of an ammoxidation reactor is disclosed in Angstadt et al., U.S. Pat. No. 4,070,393 and Gates et al., ibid, pp. 381-383, each incorporated herein by reference. The reactor contains a conventional ammoxidation catalyst, such as bismuth-molybdenum oxide, iron-antimony oxide, uranium-antimony oxide precipitated on silica and the like. Other suitable catalysts are disclosed, for example, in *Chemistry of Catalytic Processes.* Gates et al, McGraw Hill (1979) pp 349-350, and Yoshino et al, U.S. Pat. No.

3,591,620, incorporated herein by reference. Additional suitable catalysts are known to those skilled in the art.

The ammoxidation reaction is conducted at a temperature of from about 375° to 550° C., preferably from about 400° to 500° C., at low pressures, typically in the range of from about 3 to 30 psig, preferably from about 5 to 20 psig. The reactants are passed through the reactor at a relatively low velocity, typically in the range of from about 1.75 to 2.2 ft./sec. The oxygen-containing gas feed may be pure oxygen, air or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional pressure swing adsorption unit, or by mixing pure oxygen with air in the proper proportions. The ratio of oxygen to propylene in the feed is suitably in the range of from about 1.6:1 to 2.4:1 by volume. The ratio of ammonia to propylene in the feed is suitably in the range of from about 0.7 to 1.2:1 by volume.

The effluent from the ammoxidation reactor comprises a major amount of acrylonitrile and minor amounts of acrolein, hydrogen cyanide, acetonitrile, and carbon oxides and nitrogen, when present in the feed, as well as unreacted oxygen, propylene and propane. This gaseous mixture is quenched or scrubbed with a liquid, such as water, to dissolve the water-soluble compounds for subsequent separation and recovery of acrylonitrile, acetonitrile and hydrogen cyanide.

The gas phase effluent from the quench step is introduced into a pressure swing adsorption (PSA) unit. PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudo continuous flow of desired product. It is preferred to pass the quench tower effluent through a conventional dryer (not shown) to remove moisture therefrom prior to introducing it into the PSA unit.

It is may be necessary to raise the pressure of the quench tower effluent in a compressor or other suitable means prior to introducing it into the PSA unit. The compressor increases the pressure of the quench tower gaseous effluent to the operating pressure of a PSA unit, typically from about 3 to 50 psig, preferably from about 20 to 40 psig. These ranges may vary to an extent depending on the adsorbent in the PSA unit.

The adsorbent in the PSA unit may be any art-recognized material which will adsorb propane and propylene to a substantially greater degree than carbon oxides, nitrogen and oxygen, or vice versa. Silica gel or a conventional molecular sieve material, such as 4A zeolite, are preferred adsorbent materials. Silica gel is a particularly preferred material wherein oxygen-enriched air is utilized as a reactor feed material.

The PSA unit produces a recycle stream and a waste stream. The latter is comprised of oxygen, carbon oxides, i.e. carbon monoxide and carbon dioxide, nitrogen wherein the feed to the ammoxidation/oxidation reactor is air or oxygen-enriched air and $C_{1-2}$ hydrocarbons, i.e. methane, ethane and ethylene, as well as minor amounts of propane and propylene. The PSA recycle stream contains propane, propylene, a minor quantity of oxygen, typically less than about 1 percent by volume, and a minor quantity of nitrogen.

The use of an adsorbent in the PSA unit which will adsorb propane and propylene, such as a silica gel, will cause substantially all of the hydrogen in the quench tower effluent to be removed in the waste stream. Therefore, it is necessary to add an appropriate quantity of hydrogen to the recycle stream before introducing it into either the dehydrogenator or the selective oxidator. Wherein an adsorbent, which adsorbs carbon oxides, nitrogen and oxygen, such as 4A zeolite molecular sieve, is used as the adsorbent in the PSA unit, the hydrogen will be withdrawn in the recycle stream. Therefore, it will not be necessary to add hydrogen thereto. In fact, it will typically be necessary to remove some hydrogen therefrom to prevent excessive build-up in the system.

In a preferred embodiment of the subject process, a PSA system comprising parallel PSA units each containing one of the two types of adsorbers mentioned above is utilized wherein the feed is disproportionately divided between them so that the combined effluents contain the desired amount of hydrogen. The waste streams are combined and discarded. The amount of hydrogen required in the recycle feed to the dehydrogenator or the selective oxidator will vary with the catalyst and can be determined by operation of the system utilizing a given catalyst.

The selective oxidation reactor is of conventional configuration and contains an art-recognized catalyst capable of selectively catalyzing the reaction of oxygen and hydrogen to form water, i.e. the oxidation of hydrogen, carbons, i.e. propane and propylene in the PSA effluent. Such catalysts and their use are well known in the art. Suitable catalysts include noble metals or base metals, particularly platinum or palladium on alumina.

As previously stated, the oxidation reactor utilized in the present process requires only a modest capital expenditure in comparison with the multiple bed unit contemplated in the process illustrated in FIG. 2 since the PSA effluent in the subject process contains less than one percent by volume of oxygen. Typically, the oxygen content of the PSA effluent in the present process is on the order of from about 0.01 to 1 percent by volume. Since the oxygen content is at such a low level, a small oxidation reactor consisting of a single bed without the need for catalyst regeneration over a period of several years is more than adequate in the method of this invention.

Utilizing a system as shown in FIG. 3 for the production of acrylonitrile utilizing propane as the starting material, the flow rates at various points in the system were determined and are presented in Table I. The flow rates are expressed in mole percent based on 100 moles of acrylonitrile produced. The propane feed was virtually 100 percent propane. The fresh feed added to the dehydrogenator effluent prior to introduction into the ammoxidation reactor was 32.88 percent of ammonia and 67.12 percent of pure oxygen. The data expressed in Table I represents operation of the system under conditions such that 60 percent, 80 percent and 97 percent, respectively, of the propylene in the feed to the ammoxidation reactor is converted to different products, including acrylonitrile, in the ammoxidation reactor.

In Table I, Point A is the feed into the dehydrogenator after the stream from the oxidation reactor has been combined with fresh propane, Point B is the combined feed into the ammoxidation reactor, Point C is the ammoxidation reactor effluent, Point D is the quench tower gaseous effluent to the PSA unit, Point E is the recycle stream from the PSA unit and Point F is the PSA unit waste stream. As previously mentioned, the amount of hydrogen in the feed to the dehydrogenator will vary with the catalyst and reaction conditions used, and may be negligible. For purposes of the comparative results given in Tables I, II and III, hydrogen was not included in the dehydrogenator feed, Point A.

TABLE I

| Component | A | B | C | D | E | F |
|---|---|---|---|---|---|---|
| 60 Percent Conversion | | | | | | |
| Propylene | 16.6 | 20.8 | 7.7 | 15.6 | 26.5 | 3.3 |
| Propane | 79.2 | 21.5 | 19.8 | 40.4 | 66.2 | 11.2 |
| Oxygen | — | 27.8 | 5.0 | 10.2 | 0.4 | 21.3 |
| CO | — | — | 0.7 | 1.4 | 0.1 | 2.9 |
| $CO_2$ | 3.2 | 1.5 | 3.6 | 4.6 | 5.2 | 3.9 |
| Acrylonitrile | — | — | 9.9 | — | — | — |
| Acrolein | — | — | 0.1 | — | — | — |
| Acetonitrile | — | — | 0.1 | — | — | — |
| HCN | — | — | 1.5 | — | — | — |
| Water | — | — | 37.0 | — | — | — |
| Ammonia | — | 13.6 | 1.0 | — | — | — |
| Methane | 0.1 | 0.7 | 0.7 | 1.4 | 0.1 | 2.9 |
| Ethane | — | 0.2 | 0.1 | 0.3 | — | 0.6 |
| Ethylene | — | 0.2 | 0.1 | 0.3 | — | 0.6 |
| Hydrogen | 0.9 | 13.7 | 12.6 | 3.8 | 1.5 | 53.3 |
| 80 Percent Conversion | | | | | | |
| Propylene | 7.1 | 16.6 | 3.0 | 6.7 | 12.2 | 1.3 |
| Propane | 87.2 | 22.0 | 20.0 | 44.0 | 77.6 | 11.3 |
| Oxygen | — | 30.0 | 5.0 | 11.0 | 0.5 | 21.3 |
| CO | — | — | 0.7 | 1.6 | 0.1 | 3.1 |
| $CO_2$ | 4.5 | 1.9 | 4.7 | 6.4 | 7.8 | 5.0 |
| Acrylonitrile | — | — | 10.2 | — | — | — |
| Acrolein | — | — | 0.1 | — | — | — |
| Acetonitrile | — | — | 0.1 | — | — | — |
| HCN | — | — | 1.8 | — | — | — |
| Water | — | — | 39.7 | — | — | — |
| Ammonia | — | 14.4 | 1.0 | — | — | — |
| Methane | 0.1 | 0.8 | 0.7 | 1.5 | 0.1 | 2.9 |
| Ethane | — | 0.2 | 0.1 | 0.3 | — | 0.6 |
| Ethylene | — | 0.1 | 0.1 | 0.3 | — | 0.6 |
| Hydrogen | 1.0 | 14.0 | 12.8 | 28.1 | 1.7 | 53.9 |
| 97 Percent Conversion | | | | | | |
| Propylene | 1.0 | 13.8 | 0.4 | 0.8 | 1.6 | 0.2 |
| Propane | 89.9 | 21.7 | 19.4 | 44.3 | 82.0 | 10.8 |
| Oxygen | — | 32.6 | 5.0 | 11.4 | 0.5 | 21.0 |
| CO | — | — | 0.1 | 2.2 | 0.1 | 4.1 |
| $CO_2$ | 7.9 | 3.2 | 7.6 | 10.8 | 13.8 | 8.2 |
| Acrylonitrile | — | — | 9.3 | — | — | — |
| Acrolein | — | — | 0.1 | — | — | — |
| Acetonitrile | — | — | 0.1 | — | — | — |
| HCN | — | — | 2.0 | — | — | — |
| Water | — | — | 40.0 | — | — | — |
| Ammonia | — | 13.9 | 1.0 | — | — | — |
| Methane | 0.1 | 0.8 | 0.7 | 1.5 | 0.2 | 2.8 |
| Ethane | — | 0.1 | 0.1 | 0.3 | — | 0.5 |
| Ethylene | — | 0.1 | 0.1 | 0.3 | — | 0.5 |
| Hydrogen | 1.1 | 13.8 | 12.4 | 28.3 | 1.8 | 51.8 |

Again utilizing a system as shown in FIG. 3 for the production of acrylonitrile with propane as a starting material, the oxygen feed to the ammoxidation reactor was changed to an equal mixture of pure oxygen and air which produced oxygen-enriched air containing approximately 60 percent by volume of oxygen. The flow rates at various Points in the system were determined and are presented in Table II. The data expressed in Table II represents operation of the system under conditions such that 60 percent and 80 percent, respectively, of the propylene in the feed to the ammoxidation reactor is converted therein to different products, including acrylonitrile.

TABLE II

| Component | A | B | C | D | E | F |
|---|---|---|---|---|---|---|
| 60 Percent Conversion - Equal parts pure oxygen and air | | | | | | |
| Propylene | 17.4 | 12.7 | 4.8 | 7.2 | 25.9 | 0.5 |
| Propane | 76.5 | 12.7 | 12.0 | 18.0 | 64.8 | 1.2 |
| Oxygen | — | 19.4 | 5.0 | 7.5 | 0.3 | 10.1 |
| CO | — | — | 0.5 | 0.8 | — | 1.1 |
| $CO_2$ | 4.3 | 1.2 | 2.8 | 2.4 | 6.4 | 1.0 |
| Acrylonitrile | — | — | 6.0 | — | — | — |
| Acrolein | — | — | 0.1 | — | — | — |
| Acetonitrile | — | — | 0.1 | — | — | — |
| HCN | — | — | 1.2 | — | — | — |
| Water | — | — | 23.8 | — | — | — |
| Ammonia | — | 8.7 | 1.0 | — | — | — |
| Methane | — | 0.4 | 0.4 | 0.6 | 0.1 | 0.8 |
| Ethane | — | 0.1 | 0.1 | 0.1 | — | 0.2 |
| Ethylene | — | 0.1 | 0.1 | 0.1 | — | 0.2 |
| Hydrogen | 0.3 | 8.0 | 7.5 | 11.3 | 0.4 | 15.2 |
| Nitrogen | 1.3 | 36.7 | 34.6 | 51.9 | 2.0 | 69.8 |
| 80 Percent Conversion - Equal parts pure oxygen and air | | | | | | |
| Propylene | 7.4 | 9.8 | 1.9 | 2.8 | 11.7 | 0.2 |
| Propane | 85.1 | 12.8 | 12.1 | 18.4 | 76.2 | 1.2 |
| Oxygen | — | 20.2 | 5.0 | 7.6 | 0.3 | 9.8 |
| CO | — | — | 0.7 | 1.0 | — | 1.3 |
| $CO_2$ | 5.6 | 1.4 | 3.2 | 2.9 | 8.8 | 1.1 |
| Acrylonitrile | — | — | 6.0 | — | — | — |
| Acrolein | — | — | 0.1 | — | — | — |
| Acetonitrile | — | — | 0.1 | — | — | — |
| HCN | — | — | 1.3 | — | — | — |
| Water | — | — | 24.7 | — | — | — |
| Ammonia | — | 8.9 | 1.0 | — | — | — |
| Methane | 0.1 | 0.4 | 0.4 | 0.6 | 0.1 | 0.8 |
| Ethane | — | 0.1 | 0.1 | 0.1 | — | 0.2 |
| Ethylene | — | 0.1 | 0.1 | 0.1 | — | 0.2 |
| Hydrogen | 0.3 | 8.0 | 7.5 | 11.5 | 0.5 | 14.8 |
| Nitrogen | 1.5 | 38.2 | 35.9 | 54.8 | 2.4 | 70.5 |
| 60 Percent Conversion - Air | | | | | | |
| Propylene | 17.1 | 8.4 | 3.2 | 4.2 | 25.0 | 0.3 |
| Propane | 74.8 | 8.4 | 8.1 | 10.5 | 62.6 | 0.6 |
| Oxygen | — | 14.8 | 5.0 | 6.5 | 0.4 | 7.7 |
| CO | — | — | 0.4 | 0.6 | — | 0.7 |
| $CO_2$ | 4.8 | 0.9 | 2.1 | 1.6 | 7.1 | 0.6 |
| Acrylonitrile | — | — | 3.9 | — | — | — |
| Acrolein | — | — | — | — | — | — |
| Acetonitrile | — | — | — | — | — | — |
| HCN | — | — | 0.9 | — | — | — |
| Water | — | — | 16.2 | — | — | — |
| Ammonia | — | 6.1 | 1.0 | — | — | — |
| Methane | — | 0.3 | 0.3 | 0.4 | 0.1 | 0.4 |
| Ethane | — | 0.1 | 0.1 | 0.1 | — | 0.1 |
| Ethylene | — | 0.1 | 0.1 | 0.1 | — | 0.1 |
| Hydrogen | 0.3 | 5.2 | 5.0 | 6.4 | 0.4 | 7.6 |
| Nitrogen | 3.0 | 55.8 | 53.6 | 69.6 | 4.4 | 82.1 |
| 80 Percent Conversion - Air | | | | | | |
| Propylene | 7.3 | 6.5 | 1.3 | 1.6 | 11.3 | 0.1 |
| Propane | 83.5 | 8.5 | 8.2 | 10.7 | 73.9 | 0.6 |
| Oxygen | — | 15.0 | 5.0 | 6.5 | 0.5 | 7.5 |
| CO | — | — | 0.5 | 0.6 | — | 0.7 |
| $CO_2$ | 5.5 | 0.9 | 2.2 | 1.7 | 8.5 | 0.6 |
| Acrylonitrile | — | — | 4.1 | — | — | — |
| Acrolein | — | — | — | — | — | — |
| Acetonitrile | — | — | 0.1 | — | — | — |
| HCN | — | — | 0.9 | — | — | — |
| Water | — | — | 16.7 | — | — | — |
| Ammonia | — | 6.3 | 1.0 | — | — | — |
| Methane | 0.1 | 0.3 | 0.3 | 0.4 | 0.1 | 0.4 |
| Ethane | — | 0.1 | 0.1 | 0.1 | — | 0.1 |
| Ethylene | — | 0.1 | 0.1 | 0.1 | — | 0.1 |
| Hydrogen | 0.3 | 5.3 | 5.1 | 6.7 | 0.5 | 7.7 |
| Nitrogen | 3.3 | 57.0 | 54.7 | 71.6 | 5.2 | 82.3 |

Utilizing a system as shown in FIG. 2 for the production of acrylonitrile using propane as the starting material, the flow rates at various points in the system are presented in Table III. The propane, ammonia and pure oxygen feeds were as in Table I. The system was operated to convert 60, 80 and 97 percent, respectively, of the propylene feed to the ammoxidation reactor to products.

In Table III, Point A is the feed into the dehydrogenator after the recycle stream has been combined therewith, Point B is the feed into the ammoxidation reactor, Point C is the ammoxidation reactor effluent, Point D is the quench tower gaseous effluent to the selective oxidation reactor, and point E is the selective oxidation reactor effluent. During this simulation, steam was not added to the dehydrogenator feed since it is conventionally considered to have an adverse effect on the efficiency of the process. The effluent from the selective oxidation unit is divided and an appropriate fraction determined in accordance with the operating conditions of the ammoxidation reactor is introduced into a separator for the removal of carbon dioxide. It will be appreciated that Point E represents the feed into the separator as well. Point F is the effluent from the separator. In Khoobiar et al, U.S. Pat. No. 4,609,502, it is stated that a sufficient quantity of the effluent from the separator will be purged to remove the net production of carbon oxides and light hydrocarbons, Col. 3, lines 65–69. Accordingly, depending on the operating conditions of the ammoxidation reactor, from about 30 to 80 percent of the separator effluent will have to be purged. The remaining effluent is combined with the remainder of the selective oxidation effluent for reintroduction into the dehydrogenator. The combined streams are point G in Table III.

TABLE III

| Component | A | B | C | D | E | F | G |
|---|---|---|---|---|---|---|---|
| 60 Percent Conversion | | | | | | | |
| Propylene | 9.6 | 16.6 | 5.9 | 11.9 | 13.2 | 19.9 | 13.7 |
| Propane | 56.3 | 18.3 | 16.2 | 32.8 | 36.4 | 54.9 | 37.9 |
| Oxygen | — | 23.4 | 5.0 | 10.1 | — | — | — |
| CO | 4.2 | 2.2 | 2.5 | 5.1 | 5.7 | 8.5 | 5.9 |
| $CO_2$ | 9.1 | 4.9 | 6.1 | 12.3 | 13.7 | 4.1 | 13.0 |
| Acrylonitrile | — | — | 7.5 | — | — | — | — |
| Acrolein | — | — | 0.1 | — | — | — | — |
| Acetonitrile | — | — | 0.1 | — | — | — | — |
| HCN | — | — | 1.2 | — | — | — | — |
| Water | 14.6 | 7.9 | 40.7 | — | 22.5 | — | 20.8 |
| Ammonia | — | 11.1 | 1.0 | — | — | — | — |
| Methane | 4.2 | 2.9 | 2.6 | 5.2 | 6.0 | 8.7 | 6.0 |
| Ethane | 0.8 | 0.6 | 0.5 | 1.0 | 1.1 | 1.7 | 1.2 |
| Ethylene | 0.8 | 0.6 | 0.5 | 1.0 | 1.1 | 1.7 | 1.3 |
| Hydrogen | 0.2 | 11.5 | 10.1 | 20.6 | 0.3 | 0.5 | 0.3 |
| 80 Percent Conversion | | | | | | | |
| Propylene | 4.1 | 13.6 | 2.4 | 5.1 | 5.7 | 9.2 | 6.1 |
| Propane | 60.4 | 18.5 | 16.2 | 34.8 | 39.0 | 62.3 | 41.4 |
| Oxygen | — | 25.6 | 5.0 | 10.7 | — | — | — |
| CO | 4.3 | 2.1 | 2.5 | 5.4 | 6.0 | 9.7 | 6.4 |
| $CO_2$ | 10.6 | 5.4 | 7.0 | 15.0 | 16.9 | 5.4 | 15.6 |
| Acrylonitrile | — | — | 7.9 | — | — | — | — |
| Acrolein | — | — | 0.1 | — | — | — | — |
| Acetonitrile | — | — | 0.1 | — | — | — | — |
| HCN | — | — | 0.4 | — | — | — | — |
| Water | 14.6 | 7.4 | 42.8 | — | 24.0 | — | 21.5 |
| Ammonia | — | 11.9 | 1.0 | — | — | — | — |
| Methane | 4.1 | 2.7 | 2.4 | 5.1 | 5.7 | 9.1 | 6.1 |
| Ethane | 0.8 | 0.5 | 0.5 | 1.0 | 1.1 | 1.8 | 1.2 |
| Ethylene | 0.8 | 0.5 | 0.5 | 1.0 | 1.1 | 1.8 | 1.2 |
| Hydrogen | 0.3 | 11.6 | 10.2 | 21.9 | 0.4 | 0.7 | 0.5 |
| 97 Percent Conversion | | | | | | | |
| Propylene | 0.5 | 11.8 | 0.3 | 0.7 | 0.8 | 1.3 | 0.8 |
| Propane | 65.0 | 18.6 | 16.2 | 35.3 | 39.6 | 69.3 | 43.3 |
| Oxygen | — | 28.8 | 5.0 | 10.9 | — | — | — |
| CO | 4.2 | 2.0 | 2.5 | 5.6 | 6.3 | 10.9 | 6.8 |
| $CO_2$ | 12.9 | 6.1 | 9.3 | 20.3 | 22.8 | 7.9 | 21.0 |
| Acrylonitrile | — | — | 7.7 | — | — | — | — |
| Acrolein | — | — | 0.1 | — | — | — | — |
| Acetonitrile | — | — | 0.1 | — | — | — | — |
| HCN | — | — | 1.6 | — | — | — | — |
| Water | 13.3 | 6.3 | 43.8 | — | 24.5 | — | 21.5 |
| Ammonia | — | 12.0 | 1.0 | — | — | — | — |
| Methane | 2.8 | 2.0 | 1.7 | 3.7 | 4.2 | 7.3 | 4.6 |
| Ethane | 0.6 | 0.4 | 0.3 | 0.7 | 0.8 | 1.5 | 0.9 |
| Ethylene | 0.6 | 0.4 | 0.3 | 0.7 | 0.8 | 1.5 | 0.9 |
| Hydrogen | 0.1 | 11.6 | 10.1 | 22.1 | 0.2 | 0.3 | 0.2 |

The process of this invention is advantageous in that it is very efficient and is cost attractive in comparison to prior art processes. It is readily apparent from the data presented in Tables I, II and III that, in contrast to the subject process, the process illustrated in FIG. 2 continually removes propane and propylene from the system, thereby sharply reducing the efficiency thereof. It is stated in the Khoobiar et al patent that propane and propylene are removed from the purge stream before it is vented. This would require an additional sizable capital expenditure for the refrigeration equipment required for the recovery procedure as well as an on-going cost in power to operate the recovery unit. The process of the invention has a comparatively small incidence of build-up of any of the Components of the various gaseous streams formed or separated at any stage thereof. Further, the subject process can be utilized with air or an oxygen enriched air feed, heretofore not feasible with a closed loop system. Unexpectedly, the subject process operates at particularly enhanced efficiency with an oxygen enriched air feed.

The invention has been described with reference to preferred embodiments thereof. It will be appreciated by those skilled in the art that various modifications may be made from the specific details given without departing from the spirit and scope of the invention.

We claim:

1. A process for the production of alpha, beta olefinically unsaturated nitriles comprising:
   (a) forming an alkene from a gaseous alkane in a catalytic dehydrogenator;
   (b) introducing a gaseous stream comprising said alkene, pure oxygen, air or a gas-enriched in oxygen relative to air and ammonia into a suitable reactor and reacting ten in the vapor in the presence of am ammoxidation catalyst to produce a gaseous effluent containing said nitrile;
   (c) quenching said effluent in a liquid to form a liquid phase containing said nitrile and a gaseous phase;
   (d) recovering said nitrile from the liquid phase;
   (e) introducing the gaseous phase under pressure into a pressure swing adsorption unit to thereby form (i) a gaseous stream comprising said unreacted alkane and alkene, a minor amount of oxygen and nitrogen when air or oxygen-enriched air is introduced into the reactor in step (b) and (ii) a waste stream comprising oxygen, carbon monoxide, carbon dioxide, hydrocarbons lower than the reactant alkane, nitrogen, when air or oxygen-enriched air is introduced into the reactor in step (b) and minor amounts of unreacted alkane and alkene;
   (f) introducing said gaseous stream into a catalytic selective oxidation unit to remove the remaining oxygen in said stream; and
   (g) recycling the effluent from the selective oxidation unit to the dehydrogenator.

2. A process in accordance with claim 1, wherein the recycled effluent from the selective oxidation unit is combined with fresh alkane feed before introduction into the dehydrogenator.

3. A process in accordance with claim 1, wherein the alkane is propane, the alkene is propylene and the nitrile produced is acrylonitrile.

4. A process in accordance with claim 1, wherein oxygen is added in step (b) as pure oxygen.

5. A process in accordance with claim 1, wherein oxygen is added in step (b) as oxygen-enriched air containing from about 30 to about 80 percent of oxygen by volume.

6. A process in accordance with claim 5, wherein the oxygen-enriched air contains from about 55 to about 65 percent by volume of oxygen.

7. A process in accordance with claim 1, wherein the gaseous phase in step (d) is introduced into the pressure swing adsorption unit at a pressure of from about 3 to 50 psig.

8. A process in accordance with claim 1, wherein oxygen is introduced into the reactor in step (b) as oxygen-enriched air and said pressure swing adsorption unit removes substantially all of the hydrogen from the quench tower effluent and the effluent stream therefrom is combined with a hydrogen-containing stream prior to introduction into the dehydrogenator.

9. A process in accordance with claim 8, wherein the hydrogen containing stream is combined with the pressure swing absorber effluent prior to introduction into the selective oxidation unit.

10. A process in accordance with claim 1, wherein the adsorbent in the pressure swing adsorption unit is a silica gel or a molecular sieve.

11. A process in accordance with claim 1, wherein oxygen is introduced into the reactor in step (b) as pure oxygen and the effluent stream from the pressure swing adsorption unit contains substantially all of the hydrogen in the quench tower effluent and said stream is treated to remove excess hydrogen prior to recycle into the dehydrogenator.

12. A process in accordance with claim 1, wherein the temperature in the dehydrogenator is from about 500° to 800° C.

13. A process in accordance with claim 12, wherein the temperature in the dehydrogenator is from about 600° to 700° C.

14. A process in accordance with claim 1, wherein, in step (e), the gaseous phase is divided and the resultant divided streams are introduced into two pressure swing adsorption units operating in parallel, each containing a different adsorbent such that the gaseous stream formed in one of said pressure swing adsorption units contains the hydrogen in said gaseous phase, whereas the gaseous stream formed in the other pressure swing adsorption unit contains no hydrogen, wherein the gas phase is divided disproportionately between said pressure swing adsorption units so that the gaseous streams formed by said pressure swing adsorption units, when combined, contain a predetermined concentration of hydrogen.

15. A process in accordance with claim 14, wherein said pressure swing adsorption unit which produces a hydrogen-containing stream contains a 4A zeolite molecular sieve adsorbent and the other pressure swing adsorption unit contains a silica gel adsorbent.

* * * * *

UNITED STATES PATENT AND TRADEMARK OFFICE
CERTIFICATE OF CORRECTION

PATENT NO. : 4,849,538

DATED : July 18, 1989

INVENTOR(S) : R. Ramachandran, D. MacLean and D. Satchell, Jr.

It is certified that error appears in the above-identified patent and that said Letters Patent is hereby corrected as shown below:

Column 3, lines 22 and 23, after "from isobutane,", "ethylen oxide" should be deleted.

Column 6, line 39, after "oxidation of hydrogen", insert --without causing oxidation of the desired hydro- --.

Column 10, line 45 (claim 1), "ten" should be --them--.

Column 10, line 46 (claim 1), "am" should be --an--.

Signed and Sealed this

Tenth Day of December, 1991

Attest:

HARRY F. MANBECK, JR.

Attesting Officer

Commissioner of Patents and Trademarks